(12) United States Patent
Bablin

(10) Patent No.: US 6,425,850 B1
(45) Date of Patent: Jul. 30, 2002

(54) METHOD FOR DETERMINING ETA PHASE COPPER

(75) Inventor: John Matthew Bablin, Amsterdam, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/553,913

(22) Filed: Apr. 20, 2000

(51) Int. Cl.$^7$ .................................................. C07F 7/16
(52) U.S. Cl. ........................ 572/472; 423/324; 423/344; 252/182.32
(58) Field of Search ................................ 423/324, 344; 556/472; 252/182.32

(56) References Cited

U.S. PATENT DOCUMENTS

| | | | |
|---|---|---|---|
| 2,380,995 A | | 8/1945 | Rochow |
| 2,464,033 A | | 3/1949 | Gilliam |
| 4,500,724 A | | 2/1985 | Ward, III et al. |
| 4,558,017 A | * | 12/1985 | Gupta et al. ............... 423/344 |
| 5,500,399 A | | 3/1996 | Faure et al. |
| 5,817,855 A | * | 10/1998 | Langner et al. ............ 556/472 |
| 5,847,181 A | | 12/1998 | Nakauishi et al. |
| 6,005,130 A | | 12/1999 | Lewis et al. |
| 6,057,469 A | * | 5/2000 | Margaria et al. ........... 556/472 |

FOREIGN PATENT DOCUMENTS

| DE | 01B33107 | 12/1996 |
|---|---|---|
| RO | 105574 B1 | 2/1990 |

OTHER PUBLICATIONS

Rong et al., Aluminum as Promoter for the Direct Process to Methylcholorosilanes, Silicon for the Chemical Industry III, J. KR. Tuset EDS. 199 (Trondheim, Norway, 1996).

Radosavlyevich et al., Influence of Some Admixtures on the Activity of Contact Masses for Direct Synthesis of Methylchlorosilanes, Institute of Inorganic Chemistry, Belgrade, Yugoslavia, (1965).

D. Viale et al., Growth of Cu3Si from CuCl Vapor Deposition on Si(100) Oriented Wafers, 102 Journal of Crystal Growth 269–280 (1990).

"Reactivity of Commercial Silicon and Silicides Toward Copper (i) Chloride. Effect of Aluminum, Calcium and Iron on the Formation of Copper Silicide" –B. Gillot, G. Weber, H. Souha and M. Zenkouar –Journal of Alloys and Compounds 270, (1998) 275–280.

* cited by examiner

Primary Examiner—Paul F. Shaver
(74) Attorney, Agent, or Firm—Bernadette M. Bennett; Noreen C. Johnson

(57) ABSTRACT

A proportion of $Cu_3Si$ in a contact mass is determined by treating the mass with an inorganic ammonium salt, which selectively dissolves all forms of copper including free copper in deference to $Cu_3Si$, which is not dissolved. An initial copper content of the contact mass is determined, the contact mass is treated with an inorganic ammonium salt composition to extract copper in a molecular form other than $Cu_3Si$ and extracted copper is subtracted from the initial copper content.

35 Claims, 1 Drawing Sheet

METHOD FOR DETERMINING ETA PHASE COPPER

BACKGROUND OF THE INVENTION

The present invention relates to a method for determining copper content in a direct process contact mass. More particularly, the present invention relates to determining the eta phase copper content in a direct process contact mass.

Rochow, U.S. Pat. No. 2,380,995 discloses preparing a mixture of alkylhalosilanes by a direct reaction between powdered silicon and an alkylhalide in the presence of a copper-silicon alloy. This reaction is commonly referred to as the "direct method" or "direct process." The reaction can be summarized as follows:

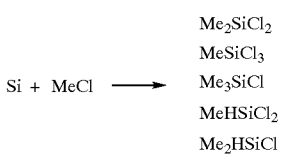

(I)

where Me is methyl.

In addition to the above methylchlorosilanes, "residue" is also formed during the production of methylchlorosilane crude. Residue means products in the methylchlorosilane crude having a boiling point greater than about 70° C., at atmospheric pressure. Residue consists of materials such as disilanes for example, symmetrical 1,1,2,2-tetrachlorodimethyldisilane; 1,1,2-trichlorotrimethyldisilane; disiloxanes; disilmethylenes; and other higher boiling species for example, trisilanes; trisiloxanes; trisilmethylenes; etc.

As shown, the alkylhalosilanes formed by the direct reaction include dimethyldichlorosilane referred to as "D" or "Di" and methyltrichlorosilane, referred to as "T" or "Tri". These are the major products of the reaction, which typically produces dimethyldichlorosilane in a range between about 80% and about 88% and methyltrichlorosilane in a range between about 5% and about 10%. Dimethyldichlorosilane has the highest commercial interest. A T/D ratio is the weight ratio of methyltrichlorosilane to dimethyldichlorosilane in the crude methylchlorosilane reaction product. An increase in the T/D ratio indicates that there is a decrease in the production of the preferred dimethyldichlorosilane. Hence, the T/D product ratio is the object of numerous improvements to the direct reaction.

Gilliam, U.S. Pat. No. 2,464,033 discloses using zinc in combination with copper catalyst as a promoter to achieve a higher selectivity of dimethyldichlorosilane. Gilliam discloses that a proportion in a range between about 2% and about 50% by weight of copper in elemental form or as the halide or oxide, and preferably 5 to 20% and zinc in a range between about 0.03% and about 0.75% by weight in the form of zinc halide, zinc oxide, or zinc metal, or mixture thereof, where the weights of copper and zinc are based on the weight of silicon, can be used as a promoter for making dialkyl substituted dihalogenosilanes, such as dimethyldichlorosilane in the direct reaction between silicon powder and methyl chloride.

Radosavlyevich et al., *Influence of Some Admixtures on the Activity of Contact Masses for Direct Synthesis of Methylchlorosilanes*, INSTITUTE OF INORGANIC CHEMISTRY, Belgrade, Yugoslavia, (1965) discloses that micro quantities of silver added to contact masses resulting from the reaction of powdered silicon and methyl chloride in the presence of cuprous chloride decreases the yield of methylchlorosilanes, while tin and calcium chloride increase the rate of formation of methylchlorosilanes.

Rong et al., *Aluminum as Promoter for the Direct Process to Methylchlorosilanes, Silicon for the Chemical Industry III*, J. KR. TUSET EDS. 199 (Trondheim, Norway, 1996) discloses adding solid aluminum compounds to improve reactivity and selectivity of the direct process. Ward et al., U.S. Pat No. 4,500,724 discloses that tin and zinc are important in improving the direct method and can be controlled to provide improved alkylhalosilane product selectivity.

Copper silicide, $Cu_3Si$ (eta phase), is a preferred form of copper and silicon in the contact mass of a direct process to provide improved selectivity. In general, factors that improve selectivity also increase the proportion of the $Cu_3Si$ form in the copper/silicon contact mass. Many of the factors that can improve the direct process and correspondingly the proportion of $Cu_3Si$ are known. However, an extent of improvement brought about by factors, either singly or in combinations of factors is not known. Methods are constantly being sought to monitor a direct process to determine the $Cu_3Si$ form of copper and silicon in the contact mass so that the combinations of factors can be determined that maximize selectivity of a direct process.

BRIEF SUMMARY OF THE INVENTION

The present invention permits monitoring of the direct process so that processing factors can be optimized for improved selectivity. According to the present invention, the proportion of $Cu_3Si$ in a contact mass can be determined by treating the mass with an inorganic ammonium salt composition, which selectively dissolves all forms of copper including free copper in deference to $Cu_3Si$, which is not dissolved. The invention relates to a method of determining a $Cu_3Si$ content of a copper and silicon contact mass, comprising determining an initial copper content of the contact mass, treating the contact mass with inorganic ammonium salt composition to extract copper in a molecular form other than $Cu_3Si$ and subtracting extracted copper from the initial copper content.

In another embodiment, an alkylhalosilane is made by forming a copper and silicon contact mass, treating the contact mass with an inorganic ammonium salt composition to extract copper in a form other than $Cu_3Si$ and effecting reaction of an alkyl halide in the presence of the treated contact mass to produce alkylhalosilane.

In still another embodiment, the present invention relates to an alkylhalosilane reaction vessel containing $Cu_3Si$ substantially free from other forms of copper. "Substantially free from other forms of copper" as used herein refers to $Cu_3Si$ present in an amount greater than about 90% by weight of the total amount of copper.

DETAILED DESCRIPTION OF THE INVENTION

Figure 1:
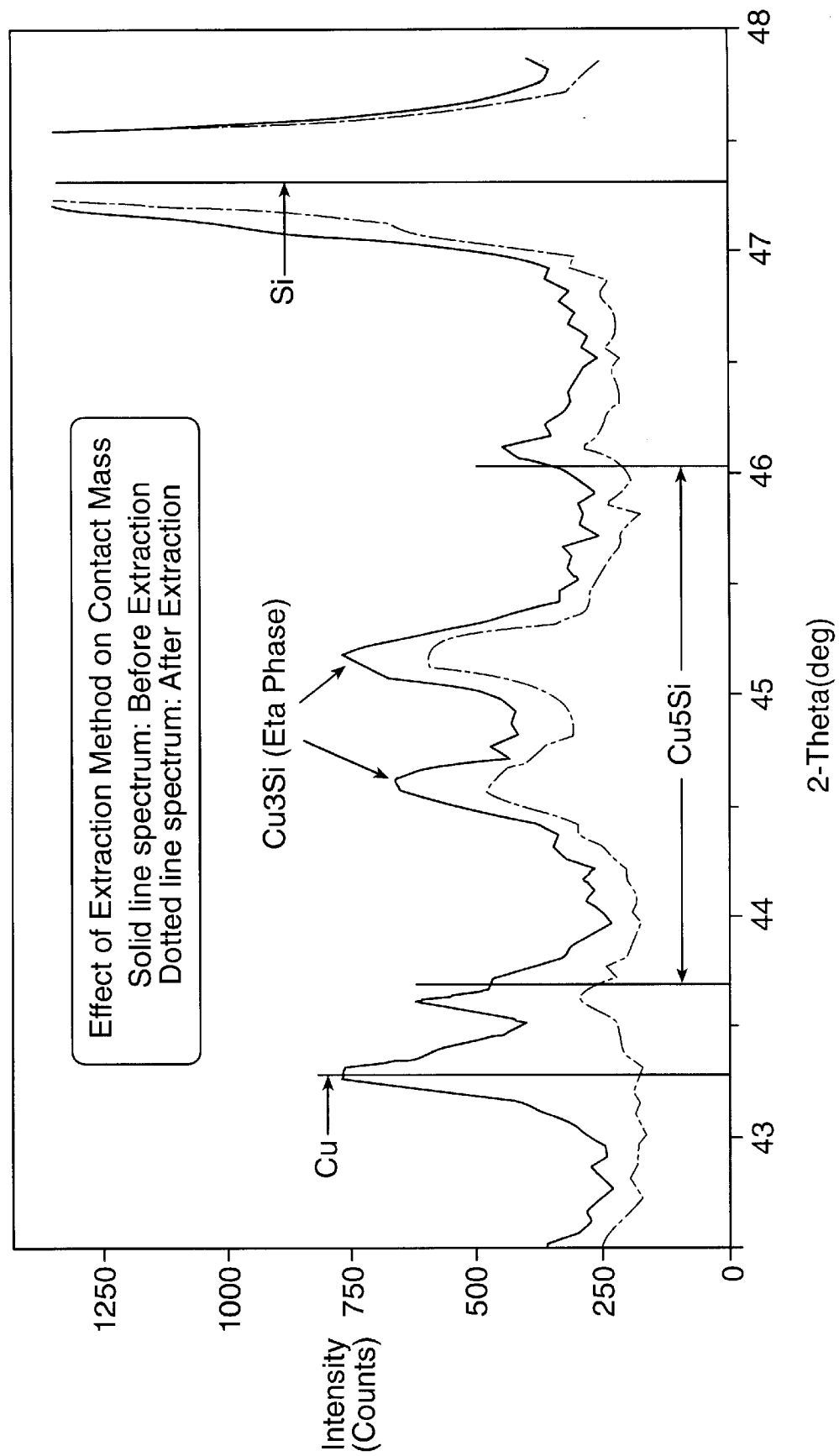
FIG. 1 shows X-ray diffraction spectrum results of copper in a contact mass.

In a typical instance, a mass for producing alkylhalosilanes is prepared by reacting silicon and cuprous chloride at a temperature in a range between about 280° C. and about 400° C. in a furnace until evolution of silicon tetrachloride ($SiCl_4$) ceases. The resulting solid contains silicon and copper and is called "contact mass." The contact mass is typically made prior to the step of contact with alkylhalide to generate alkylhalosilane. According to the present invention, a contact mass is treated with an inorganic ammonium salt composition to extract copper in a molecular form other than $Cu_3Si$. The treating step can be used to monitor the mass as an analytical tool to determine the effect of various selectivity promoters. In another embodiment, the treating step can be applied to a contact mass to improve selectivity of the mass in a direct process for producing alkylhalosilanes.

Examples of inorganic ammonium salt composition includes but are not limited to ammonium halides, ammonium sulfates, ammonium nitrates, ammonium hydroxide, or combinations thereof. Preferably, the inorganic ammonium salt composition is ammonium hydroxide. The inorganic ammonium salt composition is present in a range between about 2.5% and about 12% by weight with hydrogen peroxide in an aqueous media in a range between about 0.01% and about 0.8% by weight. The ratio of inorganic ammonium salt composition to the mass to be treated can be in a range between about 150:1 and about 2:1 in weight, preferably in a range between about 130:1 and about 3:1, and more preferably in a range between about 110:1 and about 4:1. The pH of the inorganic ammonium salt composition can be in a range between about 13.5 and about 9, preferably in a range between about 13 and about 9.5, and more preferably in a range between about 12 and about 10. The temperature of the treating step is typically in a range between about 20° C. and about 65° C., preferably in a range between about 21° C. and about 45° C., and more preferably in a range between about 22° C. and about 45° C. The time of treating can be in a range between about 10 minutes and about 75 minutes, preferably in a range between about 15 minutes and about 55 minutes, and more preferably in a range between about 20 minutes and about 45 minutes. Silicon metal and mass materials tend to be hydrophobic. Hence, the inorganic ammonium salt composition can contain a non-ionic surfactant. Additionally, the composition can include hydrogen peroxide to retain $Cu^{+2}$ in solution. The composition can include hydrogen peroxide in a range between about 0.01% and about 0.8% by weight, preferably in a range between about 0.05% and about 0.6% by weight, and more preferably in a range between about 0.1% and about 0.5% by weight. Preferably, the inorganic ammonium salt composition does not contain copper species.

The mass can be treated with an inorganic ammonium salt composition according to any convenient contact method. For example, the mass and ammonium hydroxide can be combined in a vessel and mixed by stirring or the like. Alternatively, treatment can be effected by counter-flow washing or by a temperature controlled sonication procedure as examples.

The contact mass is prepared by contacting a form of copper with silicon. The form of copper can provide a weight percent in a range between about 0.5% and about 10% copper relative to the entire contact mass. Desirably the amount of copper is in a range between about 2% and about 8% by weight and preferably in a range between about 4% and about 6% by weight. The preparation of the contact mass proceeds according to equation (II):

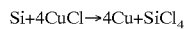

$$Si + 4CuCl \rightarrow 4Cu + SiCl_4 \qquad II$$

Carboxylic acid salts of copper can be used as the copper source to make the contact mass for the process. Copper formate, copper acetate and copper oxalate are examples of suitable carboxylic acid salts. The granular material should exhibit a BET surface area in a range between about 0.5 meters$^2$/gram and about 20 meters$^2$/gram by the nitrogen adsorption method.

Partially oxidized copper can also be the copper source to make the contact mass. Where the copper contains a level of tin relative to copper that exceeds a required range to make a satisfactory catalyst, a copper substantially free of tin can be alternated to purge excess tin, or mixtures of tin containing copper and copper substantially free of tin can be used to maintain a desired tin concentration in the resulting catalyst. An example of a partially oxidized copper that can be used to make the contact mass comprises CuO in a range between about 32% and about 33%, $Cu_2O$ in a range between about 57% and about 59%, Cu in a range between about 5% and about 10% Cu, 350 parts per million (ppm) Fe, 54 ppm Sn, 22 ppm Pb, about 0.05% insolubles and less than about 20 ppm Bi or Ti. All percentages are by weight of the total mass of the partially oxidized copper.

Particulated cupric chloride, cuprous chloride, particulated copper metal can be utilized in making the contact mass. Zinc metal, halides of zinc, for example zinc chloride and zinc oxide have been found effective as components of the copper catalyst of the mass. Tin metal dust (−325 ASTM mesh), tin halides, such as tin tetrachloride, tin oxide, tetramethyl tin, and alkyl tin halide also can be used as a source of tin for making a catalyst component of the mass.

Silicon used in the contact mass can have an iron (Fe) content in a range between about 0.1% and 1% by weight based on total silicon, calcium (Ca) content in a range between about 0.01% and 0.2% by weight based on total silicon, and an aluminum (Al) content in a range between about 0.02% and 0.5% by weight based on total silicon. The silicon typically has a particle size below about 700 microns, with an average size greater than about 20 microns and less than about 300 microns. The mean diameter of the silicon particles is preferably in the range between about 100 microns and about 150 microns. Silicon is usually obtained at a purity of at least 98% by weight of silicon and it is then comminuted to particles of silicon in the above-described range for preparation of the contact mass.

The term "selectivity" herein means the ability of a catalyst to maximize the production of dimethyldichlorosilane, as shown for example by a reduction in the value of the T/D ratio and a reduction in the % residue.

Herein, the term "effective amount," means that amount of a substance capable of either increasing the yield of the alkylhalosilane product or increasing selectivity toward dimethyldichlorosilane.

The T/D weight ratio of the methylchlorosilane reaction product is of interest. The T/D ratio is the ratio of the methyltrichlorosilane (T or Tri) to dimethyldichlorosilane (D or Di) in the crude methylchlorosilane reaction product. Accordingly, an increase in the T/D ratio indicates that there is a decrease in the production of the preferred dimethyldichlorosilane.

Although methyl chloride is preferably used in the practice of the present invention, other $C_{(1-4)}$ alkylchlorides, for example ethylchloride, propylchloride, etc, can be used. Correspondingly, the term "alkylhalosilane" includes dimethyldichlorosilane, which is the preferred methylchlorosilane, and a variety of other silanes such as tetramethylsilane, trimethylchlorosilane, methyltrichlorosilane, silicon tetrachloride, trichlorosilane, methyldichlorosilane and dimethylchlorosilane.

The alkylhalosilane reaction is typically run with a promoter such as aluminum or phosphorus. The aluminum can be added in an amount to provide to the entire contact mass in a range between about 100 parts per million (ppm) and about 1000 parts per million, and alternatively in a range between about 300 parts per million and about 700 parts per million. When phosphorus is a component of the contact mass, it is typically present in a range between about 100 parts per million and about 1000 parts per million relative to the entire contact mass. Zinc can be added in an amount in a range between about 0.01% and 1% by weight relative to the contact mass in addition to tin in an amount between about 10 and 100 parts per million.

The aluminum can be supplied from various sources. "Source" as used herein refers to the chemical compound that provides the necessary element or elements for the mass. The source of aluminum can be aluminum powder, various alloys including but not limited to copper-aluminum alloy, silver-aluminum alloy, silicon-aluminum alloy, magnesium-aluminum alloy or combinations thereof.

When phosphorus is added to the contact mass, it can be supplied from a variety of sources. For instance, the phosphorus source can be copper phosphide, zinc phosphide, phosphorus trichloride, alkylphosphines such as triethylphosphine or trimethylphosphine or combinations thereof. With or without added phosphorus, the T/D ratio decreases with the addition of the heat treated contact mass.

The present invention commonly is practiced in a fixed bed reactor or with a mass used in a fixed bed reactor. However, the process can be conducted in other types of reactors and with a mass used in other types of reactors, such as fluid bed and stirred bed. More specifically, the fixed bed reactor is a column that contains silicon particles through which alkylhalide gas passes. A stirred bed is similar to a fixed bed in which there is mechanical agitation of some sort in order to keep the bed in constant motion. A fluidized bed reactor includes a bed of silicon particles, catalyst particles and co-catalyst particles, which is fluidized; i.e., the silicon particles are suspended in the gas, typically methylchloride as it passes through the reactor. Reaction typically occurs under semi-continuous conditions or in batch mode at a temperature in a range between about 250° C. and about 350° C., and preferably in a range between about 280° C. and about 320° C. It is also advisable to carry out the reaction under a pressure in a range between about 1 atmospheres and about 10 atmospheres in instances where a fluid bed reactor is used since higher pressure increases the rate of conversion of methylchloride to methylchlorosilanes. Desirably, the pressure is in a range between about 1.1 atmospheres and about 3.5 atmospheres and preferably in a range between about 1.3 atmospheres and about 2.5 atmospheres. Methyl chloride or an inert gas such as argon or mixture thereof, can be used to fluidize the bed of silicon particles in the reactor with or without catalyst value.

The expression "semi-continuous conditions" with respect to the description of the reaction of methyl chloride and a contact mass means that reactants are added and the reactor is run until about 50% of the silicon has been utilized. After about 50% utilization, additional reactants of silicon, copper catalyst, co-catalyst and promoters may be added. With a batch mode reaction, all of the reactants are combined and reacted with any liquid or gas product until most of the reactants are consumed. In order to proceed the reaction has to be stopped and additional reactant added. A fixed bed and stirred bed are both run under batch conditions.

The process of the present invention can be used to monitor eta phase copper and correspondingly to monitor the selectivity of the alkylhalosilane reaction catalyst to determine effectiveness of selectivity improving additives in the reactors. On the other hand, the invention can also be used to treat a contact mass to improve selectivity for use of the mass in the alkylhalosilane reaction.

A contact mass of powdered silicon, with copper catalyst can be made prior to contact with methyl chloride to facilitate the generation of alkylhalosilanes. Preferably, a reactive copper compound, such as cuprous chloride, etc., can be mixed with appropriate amounts of powdered silicon, tin and zinc and heated to a temperature in a range between about 280° C. and about 400° C. The mass can then be treated with the inorganic ammonium salt to enhance eta phase copper to improve the selectivity of the alkylhalosilane reaction. Alternatively, the inorganic ammonium salt treatment can be used to monitor eta phase enhancement of the contact mass as imparted by a selectivity promoter. The contact mass of the present invention can be made by introducing the above-described components into the reactor separately or as a mixture, master batch, alloy or blend of two or more of the various components in elemental form or as compounds or mixtures and in situ monitored or treated. Alternatively, a bed can be formed and inorganic ammonium salt treated prior to charge to a reactor vessel.

Features of the invention are illustrated in the following examples, which by way of example without limitation describe preferred embodiments of the present invention.

EXAMPLE 1

Eighty (80) grams of a 5% by weight copper in silicon contact mass was prepared according to equation (II) by mixing 6.3 grams of reagent grade cuprous chloride with 76 grams of freshly ground silicon. Upon completion of contact mass formation, approximately 1000 milligrams(mg) of solid powder product, which contained 50 mg copper, was added to a beaker containing 50 mililliters(ml) of an extraction reagent, which comprised 1500 mg of ammonium hydroxide with 55 mg hydrogen peroxide and a drop of non-ionic surfactant. The solid powder was agitated by use of an external magnetic stir device for 30 to 60 minutes. Separation of solid residue from the resulting supernate was accomplished by centrifugation followed by gravimetric filtration through a 0.2 micron filter. The separated solid residue was washed with distilled water and vacuum dried. Examination of the supernate by Inductively Coupled Plasma Spectroscopy (ICP) revealed an aqueous copper concentration that was equivalent to 16 mg copper. Examination of the solid starting material by X-ray diffraction (XRD) (upper line of FIG. 1) showed a presence of copper in forms of $Cu^0$, $Cu_5Si$ and $Cu_3Si$. Examination of the residue material by XRD revealed a presence of only $Cu_3Si$ (lower line of FIG. 1). This Example shows that the ammonium hydroxide composition extracted copper except in the form of $Cu_3Si$

EXAMPLE 2

Another portion of the contact mass material prepared in Example 1 was heated in a quartz tube furnace under a flow of argon for eight hours. Upon completion of the heat treatment, approximately 1000 mg of the heat treated contact mass, which contained 50 mg copper was added to a beaker containing 50 ml of extraction reagent comprising 1500 mg of ammonium hydroxide with 55 mg hydrogen peroxide and a drop of an nonionic surfactant. The mass and reagent were agitated by use of an external magnetic stir device for 45 minutes. Separation of a solid residue and supernate was accomplished by centrifugation followed by gravimetric filtration. Examination of the supernate by ICP revealed an aqueous copper concentration that was equivalent to 0.3 mg Cu. Examination of the solid starting material by X-ray diffraction technique revealed a presence of copper only in the selectivity improving eta copper form ($CU_3Si$).

This Example illustrates monitoring of contact mass treatment by heating to improve eta copper content.

EXAMPLE 3

Phosphorus in conjunction with tin and zinc enhances dimethyldichlorosilane selectivity of a methylchlorosilane reaction. A set of experiments was conducted in which phosphorus was and was not added to a contact mass as follows.

Six grams of a silicon, copper (4.75% by weight as cuprous chloride), tin (50 ppm by weight as a dust), and zinc (0.05% by weight as dust) blend was prepared and reacted together in a fixed bed reactor under a flow of argon. In a first experiment, the temperature of the bed reached 300° C. and 3 mg of phosphorus (500 ppm by weight as triethylphosphine) were injected into the bed in four equal aliquots. In approximately 3 hours, the reaction was halted and cooled. The same experiment was repeated but without injection of phosphorous. The beds from both experiments were removed and stored under dry nitrogen conditions.

Subsequent extraction measurements as described in Example 2 were taken in triplicate using a modified ammonium hydroxide composition (with a 1:1 molar sodium acetate: acetic acid buffer solution to control and adjust the leachate pH to accommodate a cupric ion selective electrode). Approximately 250 mg to 500 mg of each bed (containing 12 mg to 24 mg of copper) were added to a beaker containing 25 ml of an extraction reagent that comprised 750 mg of ammonium hydroxide with 27 mg hydrogen peroxide and a drop of an nonionic surfactant. The beaker contents were agitated with an external magnetic stir device for 45 minutes. The beaker contents were allowed to cool to room temperature. A complexing agent comprising 1.25 N acetic acid, 1.25 M sodium acetate, 1.26 N nitric acid, $1.9e^{-1}$ M sodium nitrate and $1.03e^{-2}$ M sodium fluoride was added to each beaker to adjust pH. An Orion Cupric Ion selective electrode was used to measure aqueous copper.

The results are shown in Table 1.

TABLE 1

| Conditions | Percent Copper Extracted | Weight % $Cu_3Si$ | Standard Deviation Weight % $Cu_3Si$ |
|---|---|---|---|
| Control | 34.0 | 3.59 | 0.030 |
| Triethylphosphine | 16.7 | 4.54 | 0.011 |

Both phosphor added and phosphor-free contact masses were returned to respective reactors and used as fixed beds in a direct process. Each bed was exposed to methylchloride gas at a temperature of 300° C.

TABLE 2

| Weight % $Cu_3Si$ | D | T | Mono | MH + $M_2H$ | Residue |
|---|---|---|---|---|---|
| 3.59 | 81.83 | 5.96 | 2.98 | 1.6 | 7.65 |
| 4.54 | 85.39 | 4.42 | 2.88 | 1.0 | 6.29 |

The results reported in Table 2, show that increasing $Cu_3Si$ concentration correlates to increasing selectivity for dimethyldichlorosilane (D) at the expense of methyltrichlorosilane (T), Mono ($MeSiCl_3$), MH ($MeHSiCl_2$) and $M_2H$ ($Me_2HSiCl$) and residue.

EXAMPLE 4

This example shows the improvement of removing all but the $Cu_3Si$ phase from a contact mass. Six grams of contact mass described in Example 1 were combined with 35 mg zinc powder, and a methylchlorosilane reaction was run as in Example 3. The methylchlorosilane reaction was halted after 40% of the silicon was consumed. Of the remaining contact mass, 3.3 grams, were placed in a beaker and subjected to extraction to remove copper and $Cu_5Si$ by using 150 ml of a reagent containing 8.8 g ammonium hydroxide, 0.15 g hydrogen peroxide, and 6 drops of a non-ionic surfactant. The mixing of the contact mass and the reagent was performed for 45 minutes by means of a magnetic stirring device. Upon completion the entire content of the beaker was centrifuged for 15 minutes and a supernate was decanted. A remaining solid residue was washed with distilled water and again centrifuged. The remaining solid residue was collected and oven dried free from water after 60 minutes.

After collection of the dried solid (2 g), an additional 6 mg of zinc dust and 0.6 mg of tin dust were blended therein. A methylchlorosilane reaction was carried out with this blend as a contact mass according to the procedure of Example 3. Comparisons of final crude value of the initial contact mass to that of the initial crude value of the contact mass washed free of Cu and $Cu_5Si$ are shown in Table 3. The comparisons demonstrate the value of $CU_3Si$ in improving selectivity of the direct process. The effect of removing Cu and $CU_5Si$ from a contact mass resulted in an increase in 6.7% by weight of dimethyldichlorosilane and decreased both $M_2HSiCl$ and residue by 1.6% by weight and 4.5% by weight respectively.

TABLE 3

| Contact Mass Components | % D | % $M_2HsiCl$ | Residue | T/D |
|---|---|---|---|---|
| Cu, $Cu_5Si$, $Cu_3Si$ | 73.3 | 2.5 | 12.4 | 0.125 |
| $Cu_3Si$* | 80.0 | 0.9 | 7.9 | 0.121 |

*Extracted Cu and $Cu_5Si$ from contact mass.

While preferred embodiments of the invention have been described, the present invention is capable of variation and modification and therefore should not be limited to the precise details of the Examples. The invention includes changes and alterations that fall within the purview of the following claims.

What is claimed is:

1. A method of determining a $Cu_3Si$ content of a copper and silicon contact mass, comprising determining an initial copper content of said contact mass, treating said contact mass with an inorganic ammonium salt composition to extract copper in a molecular form other than $Cu_3Si$ and subtracting extracted copper from said initial copper content.

2. The method of claim 1, wherein said inorganic ammonium salt composition comprises ammonium hydroxide.

3. The method of claim 1, wherein said inorganic ammonium salt composition comprises inorganic ammonium salt composition in a range between about 2.5% and about 12% by weight with hydrogen peroxide in an aqueous media in a range between about 0.01% by weight and about 0.8% by weight.

4. The method of claim 1, wherein said inorganic ammonium salt composition comprises a weight ratio of inorganic ammonium salt composition to said contact mass in a range between about 150:1 and about 2:1.

5. The method of claim 1, wherein said inorganic ammonium salt composition comprises a weight ratio of inorganic ammonium salt composition to said contact mass in a range between about 130:1 and about 3:1.

6. The method of claim 1, wherein said inorganic ammonium salt composition comprises a weight ratio of inorganic ammonium salt composition to said contact mass in a range between about 110:1 and about 4:1.

7. The method of claim 1, wherein the pH of said inorganic ammonium salt composition is in a range between about 13.5 and about 9.

8. The method of claim 1, wherein the pH of said inorganic ammonium salt is in a range between about 13 and about 9.5.

9. The method of claim 1, wherein the pH of said inorganic ammonium salt is in a range between about 12 and about 10.

10. The method of claim 1, wherein said contact mass is treated with said inorganic ammonium salt composition at a temperature in a range between about 20° C. and about 65° C.

11. The method of claim 1, wherein said contact mass is treated with said inorganic ammonium salt composition at a temperature in a range between about 21° C. and about 45° C.

12. The method of claim 1, wherein said contact mass is treated with said inorganic ammonium salt composition at a temperature in a range between about 22° C. and about 45° C.

13. The method of claim 1, wherein said contact mass is treated with said inorganic ammonium salt composition at a temperature in a range between about 20° C. and about 65° C. for a period of time in a range between about 10 minutes and about 75 minutes.

14. The method of claim 1, wherein said contact mass is treated with said inorganic ammonium salt composition at a temperature in a range between about 20° C. and about 65° C. for a period of time in a range between about 15 minutes and about 55 minutes.

15. The method of claim 1, wherein said contact mass is treated with said inorganic ammonium salt composition at a temperature in a range between about 20° C. and about 65° C. for a period of time in a range between about 20 minutes and about 45 minutes.

16. The method of claim 1, wherein said inorganic ammonium salt composition comprises a non-ionic surfactant.

17. The method of claim 1, wherein said inorganic ammonium salt composition comprises hydrogen peroxide in a range between about 0.01% by weight and about 0.8% by weight.

18. The method of claim 1, wherein said inorganic ammonium salt composition comprises hydrogen peroxide in a range between about 0.05% by weight and about 0.6% by weight.

19. The method of claim 1, wherein said inorganic ammonium salt composition comprises hydrogen peroxide in a range between about 0.1% by weight and about 0.5% by weight.

20. A method to monitor selectivity of a copper and silicon contact mass used to make an alkylhalosilane, comprising determining an initial copper content, treating with an inorganic ammonium salt and subtracting extracted copper from said initial copper content according to claim 1.

21. The method of claim 1, wherein said contact mass is treated by mixing and stirring with said inorganic ammonium salt, by counter-flow washing with said inorganic ammonium salt composition or by a temperature controlled sonication procedure with said inorganic ammonium salt composition.

22. The method of claim 1, wherein said mass comprises powdered silicon and a copper-zinc-tin catalyst.

23. The method of claim 1, wherein said treating with inorganic ammonium salt composition increases a $Cu_3Si$ form of copper in said contact mass.

24. The method of claim 1, wherein said contact mass comprises copper in a range between about 0.5% by weight and about 10% by weight relative to the entire contact mass.

25. The method of claim 1, wherein said contact mass comprises copper in a range between about 2% by weight and about 8% by weight relative to the entire contact mass.

26. The method of claim 1, wherein said contact mass comprises copper in a range between about 4% by weight and about 6% by weight relative to the entire contact mass.

27. A method for making an alkylhalosilane comprising forming a copper and silicon contact mass, treating the contact mass with ammonium hydroxide composition to extract copper in a form other than $Cu_3Si$ and effecting reaction between an alkyl halide and silicon in the presence of said treated contact mass to produce alkylhalosilane.

28. An alkylhalosilane reaction vessel containing a copper and silicon contact mass comprising $Cu_3Si$ substantially free from other forms of copper.

29. The vessel of claim 28, wherein said contact mass comprises powdered silicon and a copper-zinc-tin catalyst.

30. The vessel of claim 28, wherein said contact mass comprises copper in a range between about 0.5% by weight and about 10% by weight relative to the entire contact mass.

31. The vessel of claim 28, wherein said contact mass comprises copper in a range between about 2% by weight and about 8% by weight relative to the entire contact mass.

32. The vessel of claim 28, wherein said contact mass comprises copper in a range between about 4% by weight to 6% by weight relative to the entire contact mass.

33. The vessel of claim 28, comprising a fluid-bed reactor.

34. The vessel of claim 28, comprising a fixed-bed reactor.

35. The vessel of claim 28, comprising a stirred-bed reactor.

* * * * *